US008292926B2

(12) United States Patent
Jackson

(10) Patent No.: US 8,292,926 B2
(45) Date of Patent: Oct. 23, 2012

(54) DYNAMIC STABILIZATION CONNECTING MEMBER WITH ELASTIC CORE AND OUTER SLEEVE

(76) Inventor: Roger P. Jackson, Prairie Village, KS (US)

( * ) Notice: Subject to any disclaimer, the term of this patent is extended or adjusted under 35 U.S.C. 154(b) by 482 days.

(21) Appl. No.: 11/894,001

(22) Filed: Aug. 17, 2007

(65) Prior Publication Data

US 2007/0293862 A1    Dec. 20, 2007

Related U.S. Application Data

(63) Continuation-in-part of application No. 11/522,503, filed on Sep. 14, 2006.

(60) Provisional application No. 60/851,353, filed on Oct. 12, 2006, provisional application No. 60/905,472, filed on Mar. 7, 2007, provisional application No. 60/722,300, filed on Sep. 30, 2005, provisional application No. 60/725,445, filed on Oct. 11, 2005, provisional application No. 60/728,912, filed on Oct. 21, 2005, provisional application No. 60/736,112, filed on Nov. 10, 2005, provisional application No. 60/832,644, filed on Jul. 21, 2006.

(51) Int. Cl.
*A61B 17/70* (2006.01)

(52) U.S. Cl. ........................ 606/257; 606/255

(58) Field of Classification Search .................. 606/916, 606/266, 278, 279, 254, 246, 264, 308, 326, 606/86 A, 301, 302, 305, 255
See application file for complete search history.

(56) References Cited

U.S. PATENT DOCUMENTS

| | | | |
|---|---|---|---|
| 2,243,717 A | 5/1941 | Moreira | |
| 3,236,275 A | 2/1966 | Smith | |
| 3,604,487 A | 9/1971 | Gilbert | |
| 3,640,416 A | 2/1972 | Temple | |
| 4,041,939 A | 8/1977 | Hall | |
| 4,373,754 A | 2/1983 | Bollfrass et al. | |
| 4,448,191 A | 5/1984 | Rodnyansky et al. | |
| 4,484,570 A | 11/1984 | Sutter et al. | |
| 4,600,224 A | 7/1986 | Blose | |
| 4,611,581 A * | 9/1986 | Steffee .......................... | 606/292 |
| 4,653,486 A | 3/1987 | Coker | |
| 4,703,954 A | 11/1987 | Ortloff et al. | |
| 4,707,001 A | 11/1987 | Johnson | |
| 4,743,260 A | 5/1988 | Burton | |
| 4,748,260 A | 5/1988 | Marlett | |
| 4,836,196 A | 6/1989 | Park et al. | |

(Continued)

FOREIGN PATENT DOCUMENTS

DE    G9202745.8    4/1992

(Continued)

OTHER PUBLICATIONS

*EBI Omega 21* Brochure, EBI Spine Systems, pub. 1999.

(Continued)

*Primary Examiner* — Pedro Philogene
(74) *Attorney, Agent, or Firm* — John C. McMahon

(57) ABSTRACT

A dynamic fixation medical implant having at least two bone anchors includes a longitudinal connecting member assembly having an elongate core and an outer sleeve. The core is of one-piece construction, elastic, and includes end portions for attachment to the bone anchors. The outer sleeve may include compression grooves. The sleeve surrounds the core and extends between the pair of bone anchors, the sleeve being compressible between the bone anchors.

20 Claims, 4 Drawing Sheets

U.S. PATENT DOCUMENTS

| | | |
|---|---|---|
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,022,791 A | 6/1991 | Isler |
| 5,034,011 A | 7/1991 | Howland |
| 5,067,955 A | 11/1991 | Cotrel |
| 5,092,635 A | 3/1992 | DeLange et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,507,745 A | 4/1996 | Logroscino et al. |
| 5,540,688 A | 7/1996 | Navas |
| 5,545,165 A | 8/1996 | Biedermann et al. |
| 5,554,157 A | 9/1996 | Errico et al. |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A * | 9/1997 | Martin ................ 606/86 A |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| RE36,221 E | 6/1999 | Breard et al. |
| 5,944,465 A | 8/1999 | Janitzki |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,143,032 A | 11/2000 | Schafer et al. |
| 6,146,383 A | 11/2000 | Studer et al. |
| 6,183,472 B1 | 2/2001 | Lutz |
| 6,187,005 B1 | 2/2001 | Brace et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,241,730 B1 | 6/2001 | Alby |
| 6,248,105 B1 | 6/2001 | Schlapfer et al. |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,331,179 B1 | 12/2001 | Freid et al. |
| 6,355,040 B1 | 3/2002 | Richelsoph et al. |

| | | | | | | |
|---|---|---|---|---|---|---|
| RE37,665 E | 4/2002 | Ralph et al. | 6,802,844 B2 | 10/2004 | Ferree | |
| 6,368,321 B1 | 4/2002 | Jackson | 6,827,719 B2 | 12/2004 | Ralph et al. | |
| 6,402,752 B2 | 6/2002 | Schäffler-Wachter et al. | 6,830,571 B2 | 12/2004 | Lenke et al. | |
| 6,402,757 B1 | 6/2002 | Moore et al. | 6,835,196 B2 | 12/2004 | Biedermann et al. | |
| 6,440,137 B1 | 8/2002 | Horvath et al. | 6,837,889 B2 | 1/2005 | Shluzas | |
| 6,451,021 B1 | 9/2002 | Ralph et al. | 6,840,940 B2 | 1/2005 | Ralph et al. | |
| 6,471,703 B1 | 10/2002 | Ashman | 6,843,791 B2 | 1/2005 | Serhan | |
| 6,471,705 B1 | 10/2002 | Biedermann et al. | 6,858,031 B2 | 2/2005 | Morrison et al. | |
| 6,485,491 B1 | 11/2002 | Farris et al. | 6,869,432 B2 | 3/2005 | Schlapfer et al. | |
| 6,485,492 B1 | 11/2002 | Halm et al. | 6,869,433 B2 | 3/2005 | Glascott | |
| 6,485,494 B1 | 11/2002 | Haider | 6,872,208 B1 | 3/2005 | McBride et al. | |
| 6,488,681 B2 | 12/2002 | Martin et al. | 6,896,676 B2 | 5/2005 | Zubok et al. | |
| 6,508,818 B2 | 1/2003 | Steiner et al. | 6,932,817 B2 | 8/2005 | Baynham et al. | |
| 6,520,962 B1 | 2/2003 | Taylor et al. | 6,932,820 B2 | 8/2005 | Osman | |
| 6,527,804 B1 | 3/2003 | Gauchet et al. | 6,945,972 B2 | 9/2005 | Frigg et al. | |
| 6,530,929 B1 | 3/2003 | Justis et al. | 6,953,462 B2 | 10/2005 | Liebermann | |
| 6,533,786 B1 | 3/2003 | Needham et al. | 6,955,677 B2 | 10/2005 | Dahners | |
| 6,540,749 B2 | 4/2003 | Schafer et al. | 6,958,065 B2 | 10/2005 | Ueyama et al. | |
| 6,547,790 B2 | 4/2003 | Harkey, III et al. | 6,964,664 B2 | 11/2005 | Freid et al. | |
| 6,551,320 B2 | 4/2003 | Lieberman | 6,964,665 B2 | 11/2005 | Thomas et al. | |
| 6,551,323 B2 | 4/2003 | Doubler et al. | 6,964,667 B2 | 11/2005 | Shaolian et al. | |
| 6,554,831 B1 | 4/2003 | Rivard et al. | 6,966,910 B2 | 11/2005 | Ritland | |
| 6,554,832 B2 | 4/2003 | Shluzas | 6,974,460 B2 | 12/2005 | Carbone et al. | |
| 6,554,834 B1 | 4/2003 | Crozet et al. | 6,979,334 B2 | 12/2005 | Dalton | |
| 6,558,387 B2 | 5/2003 | Errico et al. | 6,981,973 B2 | 1/2006 | McKinley | |
| 6,562,040 B1 | 5/2003 | Wagner | 6,986,771 B2 | 1/2006 | Paul et al. | |
| 6,565,565 B1 | 5/2003 | Yuan et al. | 6,989,011 B2 | 1/2006 | Paul et al. | |
| 6,565,567 B1 | 5/2003 | Haider | 6,991,632 B2 | 1/2006 | Ritland | |
| 6,582,436 B2 | 6/2003 | Schlapfer et al. | RE39,035 E | 3/2006 | Finn et al. | |
| 6,582,466 B1 | 6/2003 | Gauchet | 7,008,424 B2 | 3/2006 | Teitelbaum | |
| 6,585,740 B2 | 7/2003 | Schlapfer et al. | 7,018,378 B2 | 3/2006 | Biedermann et al. | |
| 6,595,992 B1 | 7/2003 | Wagner et al. | 7,018,379 B2 | 3/2006 | Drewry et al. | |
| 6,595,993 B2 | 7/2003 | Donno et al. | 7,029,475 B2 | 4/2006 | Panjabi | |
| 6,610,063 B2 | 8/2003 | Kumar et al. | 7,125,410 B2 | 10/2006 | Freudiger | |
| 6,613,050 B1 | 9/2003 | Wagner et al. | 7,137,985 B2 | 11/2006 | Jahng | |
| 6,623,485 B2 | 9/2003 | Doubler et al. | 7,611,518 B2 * | 11/2009 | Walder et al. | 606/86 A |
| 6,626,907 B2 | 9/2003 | Campbell et al. | 7,618,444 B2 * | 11/2009 | Shluzas | 606/279 |
| 6,626,908 B2 | 9/2003 | Cooper et al. | 7,621,912 B2 * | 11/2009 | Harms et al. | 606/59 |
| 6,635,059 B2 | 10/2003 | Randall et al. | 7,651,515 B2 * | 1/2010 | Mack et al. | 606/254 |
| 6,648,885 B1 | 11/2003 | Friesem | 7,722,649 B2 * | 5/2010 | Biedermann et al. | 606/257 |
| 6,648,887 B2 | 11/2003 | Ashman | 7,850,715 B2 * | 12/2010 | Banouskou et al. | 606/246 |
| 6,652,765 B1 | 11/2003 | Beaty | 2001/0001119 A1 | 5/2001 | Lombardo | |
| 6,656,179 B1 | 12/2003 | Schaefer et al. | 2001/0037111 A1 | 11/2001 | Dixon et al. | |
| 6,656,181 B2 | 12/2003 | Dixon et al. | 2002/0007184 A1 | 1/2002 | Ogilvie et al. | |
| 6,660,004 B2 | 12/2003 | Barker et al. | 2002/0013586 A1 | 1/2002 | Justis et al. | |
| 6,663,632 B1 | 12/2003 | Frigg | 2002/0035366 A1 | 3/2002 | Walder et al. | |
| 6,663,635 B2 | 12/2003 | Frigg et al. | 2002/0045898 A1 | 4/2002 | Freid et al. | |
| 6,673,073 B1 | 1/2004 | Schafer | 2002/0058942 A1 | 5/2002 | Biedermann et al. | |
| 6,676,661 B1 | 1/2004 | Benlloch et al. | 2002/0082602 A1 | 6/2002 | Biedermann et al. | |
| 6,679,833 B2 | 1/2004 | Smith et al. | 2002/0111626 A1 | 8/2002 | Ralph et al. | |
| 6,682,529 B2 | 1/2004 | Stahurski | 2002/0143341 A1 | 10/2002 | Biedermann et al. | |
| 6,682,530 B2 | 1/2004 | Dixon et al. | 2002/0173789 A1 | 11/2002 | Howland | |
| 6,689,133 B2 | 2/2004 | Morrison et al. | 2002/0193795 A1 | 12/2002 | Gertzbein et al. | |
| 6,689,134 B2 | 2/2004 | Ralph et al. | 2003/0023243 A1 | 1/2003 | Biedermann et al. | |
| 6,695,843 B2 | 2/2004 | Biedermann et al. | 2003/0073996 A1 | 4/2003 | Doubler et al. | |
| 6,695,851 B2 | 2/2004 | Zdeblick et al. | 2003/0083657 A1 | 5/2003 | Drewry et al. | |
| 6,699,249 B2 | 3/2004 | Schlapfer et al. | 2003/0093078 A1 | 5/2003 | Ritland | |
| 6,706,045 B2 | 3/2004 | Lin et al. | 2003/0100896 A1 | 5/2003 | Biedermann et al. | |
| 6,712,818 B1 | 3/2004 | Michelson | 2003/0105460 A1 | 6/2003 | Crandall et al. | |
| 6,716,213 B2 | 4/2004 | Shitoto | 2003/0109880 A1 | 6/2003 | Shirado et al. | |
| 6,716,214 B1 | 4/2004 | Jackson | 2003/0114852 A1 | 6/2003 | Biedermann et al. | |
| 6,716,247 B2 | 4/2004 | Michelson | 2003/0125741 A1 | 7/2003 | Biedermann et al. | |
| 6,723,100 B2 | 4/2004 | Biedermann et al. | 2003/0149432 A1 | 8/2003 | Frigg et al. | |
| 6,730,093 B2 | 5/2004 | Saint Martin | 2003/0163133 A1 | 8/2003 | Altarac et al. | |
| 6,730,127 B2 | 5/2004 | Michelson | 2003/0171749 A1 | 9/2003 | Le Couedic et al. | |
| 6,733,502 B2 | 5/2004 | Altarac et al. | 2003/0176862 A1 | 9/2003 | Taylor et al. | |
| 6,736,816 B2 | 5/2004 | Ritland | 2003/0191470 A1 | 10/2003 | Ritland | |
| 6,736,820 B2 | 5/2004 | Biedermann et al. | 2003/0199873 A1 | 10/2003 | Richelsoph | |
| 6,740,086 B2 | 5/2004 | Richelsoph | 2003/0208204 A1 | 11/2003 | Bailey et al. | |
| 6,746,449 B2 | 6/2004 | Jones et al. | 2003/0216735 A1 | 11/2003 | Altarac et al. | |
| 6,755,829 B1 | 6/2004 | Bono et al. | 2003/0220642 A1 | 11/2003 | Freudiger | |
| 6,755,835 B2 | 6/2004 | Schultheiss et al. | 2004/0002708 A1 | 1/2004 | Ritland | |
| 6,755,836 B1 | 6/2004 | Lewis | 2004/0006342 A1 | 1/2004 | Altarac et al. | |
| 6,761,723 B2 | 7/2004 | Buttermann et al. | 2004/0049189 A1 | 3/2004 | Le Couedic et al. | |
| 6,767,351 B2 | 7/2004 | Orbay et al. | 2004/0049190 A1 | 3/2004 | Biedermann et al. | |
| 6,770,075 B2 * | 8/2004 | Howland | 606/86 A | 2004/0073215 A1 | 4/2004 | Carli | |
| 6,780,186 B2 | 8/2004 | Errico et al. | 2004/0078082 A1 | 4/2004 | Lange | |
| 6,783,527 B2 | 8/2004 | Drewry et al. | 2004/0087949 A1 | 5/2004 | Bono et al. | |
| 6,790,209 B2 | 9/2004 | Beale et al. | 2004/0087952 A1 | 5/2004 | Borgstrom et al. | |

| | | |
|---|---|---|
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065515 A1 | 3/2005 | Jahng |
| 2005/0065516 A1 | 3/2005 | Jahng |
| 2005/0070899 A1 | 3/2005 | Doubler et al. |
| 2005/0080415 A1 | 4/2005 | Keyer et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251140 A1 | 11/2005 | Shaolian et al. |
| 2005/0251141 A1 | 11/2005 | Frigg et al. |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Liebermann |
| 2006/0009770 A1 | 1/2006 | Speirs et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0079896 A1 | 4/2006 | Kwak |
| 2006/0079898 A1 | 4/2006 | Ainsworth |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084991 A1 | 4/2006 | Borgstrom |
| 2006/0085069 A1 | 4/2006 | Kim |
| 2006/0106381 A1 | 5/2006 | Ferree |
| 2006/0122599 A1 | 6/2006 | Drewry |
| 2006/0129239 A1 | 6/2006 | Kwak |
| 2006/0142758 A1 | 6/2006 | Petit |
| 2006/0142760 A1 | 6/2006 | McDonnell |
| 2006/0149228 A1 | 7/2006 | Schlapfer |
| 2006/0149229 A1 | 7/2006 | Kwak |
| 2006/0184171 A1 | 8/2006 | Biedermann |
| 2006/0184180 A1 | 8/2006 | Augostino |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0200130 A1 | 9/2006 | Hawkins |
| 2006/0212033 A1 | 9/2006 | Rothman |
| 2006/0229608 A1 | 10/2006 | Foster |

| | | | | | | |
|---|---|---|---|---|---|---|
| 2006/0229609 | A1 | 10/2006 | Wang | FR | 2718946 | 10/1995 |
| 2006/0229612 | A1 | 10/2006 | Rothman | FR | 2729291 | 7/1996 |
| 2006/0229613 | A1 | 10/2006 | Timm | FR | 2796545 | 1/2001 |
| 2006/0241599 | A1 | 10/2006 | Konieczynski et al. | FR | 2799949 | 4/2001 |
| 2006/0241769 | A1 | 10/2006 | Gordon | FR | 2856578 | 6/2003 |
| 2006/0241771 | A1 | 10/2006 | Gordon | FR | 2865373 | 1/2004 |
| 2006/0247632 | A1 | 11/2006 | Winslow | FR | 2865375 | 1/2004 |
| 2006/0247633 | A1 | 11/2006 | Winslow | FR | 2865377 | 1/2004 |
| 2006/0247635 | A1 | 11/2006 | Gordon | FR | 2857850 | 4/2004 |
| 2006/0247637 | A1 | 11/2006 | Colleran | FR | 2865378 | 10/2004 |
| 2006/0247779 | A1 | 11/2006 | Gordon | GB | 2365345 | 2/2002 |
| 2006/0264935 | A1 | 11/2006 | White | GB | 2382304 | 5/2003 |
| 2006/0264937 | A1 | 11/2006 | White | JP | 2000325358 | 3/2000 |
| 2006/0264940 | A1 | 11/2006 | Hartmannt | WO | WO92/03100 | 3/1992 |
| 2006/0276789 | A1 | 12/2006 | Jackson | WO | WO94/10927 | 5/1994 |
| 2006/0282075 | A1 | 12/2006 | Labrom | WO | WO94/26191 | 11/1994 |
| 2006/0282076 | A1 | 12/2006 | Labrom | WO | WO01/45576 | 6/2001 |
| 2006/0282077 | A1 | 12/2006 | Labrom | WO | WO02/054966 | 7/2002 |
| 2006/0282078 | A1 | 12/2006 | Labrom | WO | WO02/102259 | 12/2002 |
| 2006/0282079 | A1 | 12/2006 | Labrom | WO | WO03/026523 | 4/2003 |
| 2006/0282080 | A1 | 12/2006 | Albert | WO | WO03/068088 | 8/2003 |
| 2006/0293657 | A1 | 12/2006 | Hartmann | WO | WO2004/041100 | 5/2004 |
| 2006/0293663 | A1 | 12/2006 | Walkenhorst | WO | WO2004/075778 | 9/2004 |
| 2007/0005062 | A1 | 1/2007 | Lange | WO | WO2004/089245 | 10/2004 |
| 2007/0005063 | A1 | 1/2007 | Bruneau | WO | WO2004/107997 | 12/2004 |
| 2007/0005137 | A1 | 1/2007 | Kwak | WO | WO2005/000136 | 1/2005 |
| 2007/0016190 | A1 | 1/2007 | Martinez | WO | WO2005/000137 | 1/2005 |
| 2007/0016193 | A1 | 1/2007 | Ritland | WO | WO2005/020829 | 3/2005 |
| 2007/0043356 | A1 | 2/2007 | Timm | WO | WO2005/065374 | 7/2005 |
| 2007/0049936 | A1 | 3/2007 | Colleran | WO | WO2005/065375 | 7/2005 |
| 2007/0055236 | A1 | 3/2007 | Hudgins | WO | WO2005/072632 | 8/2005 |
| 2007/0055247 | A1 | 3/2007 | Jahng | WO | WO2005/082262 | 9/2005 |
| 2007/0073289 | A1 | 3/2007 | Kwak | WO | WO2005/099400 | 10/2005 |
| 2007/0073293 | A1 | 3/2007 | Martz | WO | WO2005/104969 | 11/2005 |
| 2007/0233085 | A1 * | 10/2007 | Biedermann et al. ............ 606/61 | WO | WO2006/012088 | 2/2006 |
| | | | | WO | WO2006/017616 | 2/2006 |
| FOREIGN PATENT DOCUMENTS | | | | WO | WO2006/028537 | 3/2006 |
| DE | 4425392 | 11/1995 | | | | |
| DE | 19509141 | 9/1996 | | | | |
| DE | 19509331 | 9/1996 | | | | |
| DE | 29806563 | 7/1998 | | | | |
| DE | 29810798 | 12/1999 | | | | |
| DE | 19951145 | 5/2001 | | | | |
| EP | 0667127 | 8/1995 | | | | |
| EP | 0677277 | 10/1995 | | | | |
| EP | 0885598 | 12/1998 | | | | |
| EP | 1121902 | 8/2001 | | | | |
| EP | 1190678 | 3/2002 | | | | |
| EP | 1570795 | 2/2005 | | | | |
| EP | 1570795 | 9/2005 | | | | |
| EP | 1579816 | 9/2005 | | | | |
| EP | 1634537 | 3/2006 | | | | |
| FR | 2717370 | 9/1995 | | | | |

OTHER PUBLICATIONS

*Claris Instrumentation* Brochure, G Med, pub. 1997.
*VLS System Variable Locking Screw* Brochure, Interpore Cross International, 1999.
*The Rod Plate System* Brochure, Stryker Howmedica Osteonics, pub. Oct. 1999.
*SDRS Surgical Dynamics Rod System* Brochure, Surgical Dynamics, pub. 1998-99.
*Versalok Low Back Fixation System* Brochure, Wright Medical Technology, Inc., pub. 1997.
Brochure of Tyco/Healthcare/Surgical Dynamics on Spiral Radius 90D, Publication Date: Sep. 2001, pp. 1-8.

\* cited by examiner

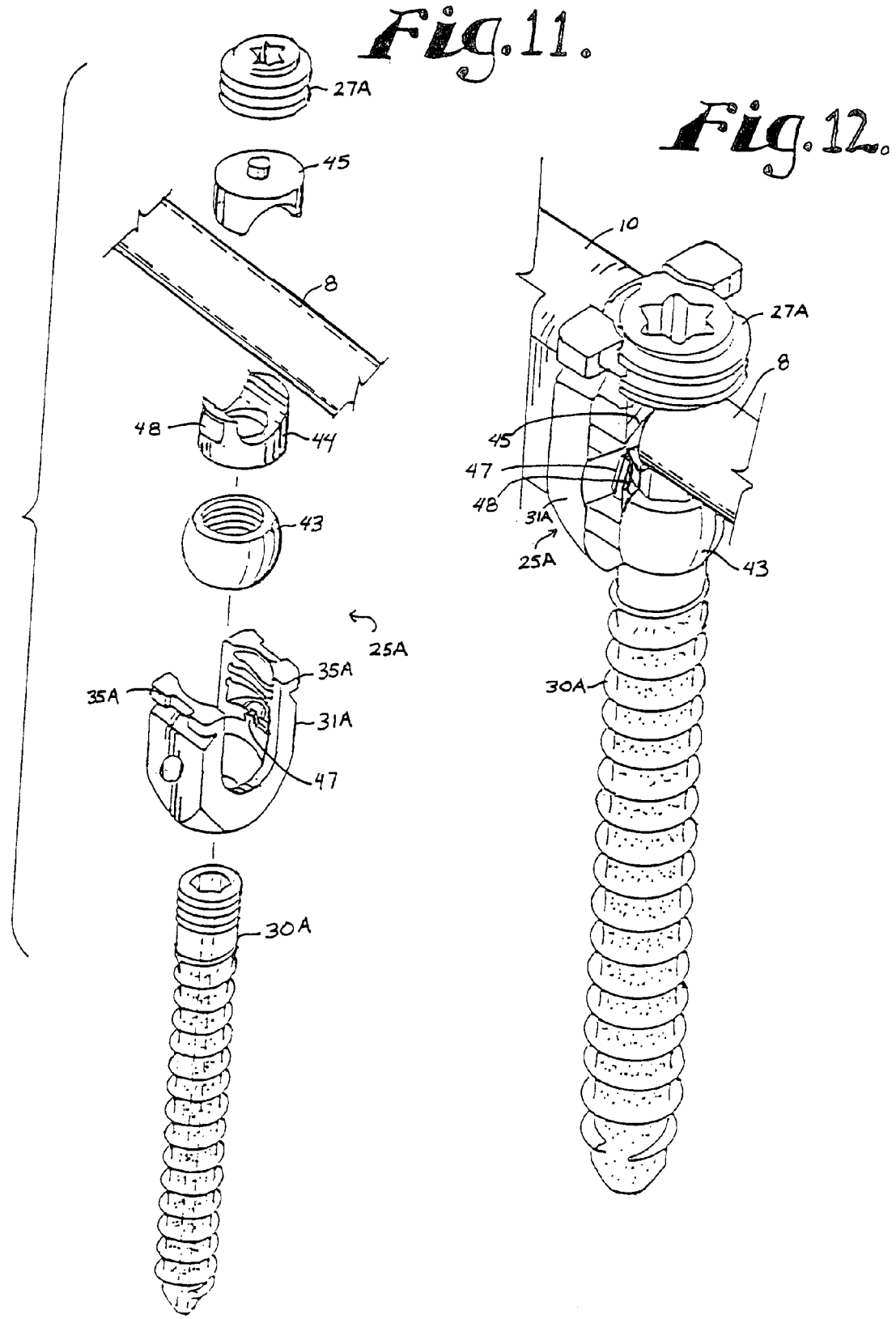

DYNAMIC STABILIZATION CONNECTING MEMBER WITH ELASTIC CORE AND OUTER SLEEVE

CROSS REFERENCE TO RELATED APPLICATION

This application claims the benefit of U.S. Provisional Application No. 60/851,353, filed Oct. 12, 2006, the disclosure of which is incorporated by reference herein. This application also claims the benefit of U.S. Provisional Application No. 60/905,472, filed Mar. 7, 2007, the disclosure of which is incorporated by reference herein. This application is also a continuation-in-part of U.S. patent application Ser. No. 11/522,503, filed Sep. 14, 2006 that claims the benefit of U.S. Provisional Application Nos. 60/722,300, filed Sep. 30, 2005; 60/725,445, filed Oct. 11, 2005; 60/728,912, filed Oct. 21, 2005; 60/736,112, filed Nov. 10, 2005, and 60/832,644, filed Jul. 21, 2006; the disclosures all of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

Fusion, however, has some undesirable side effects. One apparent side effect is the immobilization of a portion of the spine. Furthermore, although fusion may result in a strengthened portion of the spine, it also has been linked to more rapid degeneration and even hyper-mobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Problems may arise with such devices, however, including tissue scarring, lack of adequate spinal support and lack of fatigue strength or endurance limit. Fatigue strength has been defined as the repeated loading and unloading of a specific stress on a material structure until it fails. Fatigue strength can be tensile or distraction, compression, shear, torsion, bending, or a combination of these.

Another type of soft or dynamic system known in the art includes bone anchors connected by flexible cords or strands, typically made from a synthetic polymer material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems require specialized fixed or non-polyaxial bone anchors as well as tooling for tensioning and holding the cord or strand in the bone anchors. Although flexible, the cords or strands utilized in such systems do not allow for elastic distraction or stretchability of the system once implanted because the cord or strand must be stretched or pulled to maximum tension during installation in order to provide a stable, supportive system. In addition, because the bone anchors are fixed and not polyaxial they are more difficult to use.

The complex dynamic conditions associated with spinal movement therefore provide quite a challenge for the design of more flexible elongate longitudinal connecting members that exhibit an adequate fatigue strength to provide stabilization and protected motion of the spine, without fusion, and allow for some natural movement of the portion of the spine being reinforced and supported by the elongate flexible connecting member.

SUMMARY OF THE INVENTION

Longitudinal connecting member assemblies according to the invention for use between at least two bone anchors provide dynamic, protected motion of the spine. A longitudinal connecting member assembly according to the invention has an inner elastic core. An outer sleeve or spacer surrounds the core, the sleeve extending between a pair of adjacent bone anchors. The elastic core and outer sleeve cooperate dynamically, both features having some elasticity and flexibility, with the outer sleeve primarily protecting and limiting flexing or bending movement of the inner core. The inner core can be of varying degrees of firmness and of any cross-sectional shape. The outer sleeve may include a grooved portion facilitating compression of the sleeve against the pair of bone anchors upon installation therebetween. The outer sleeve also can be of varying degrees of firmness and of any cross-sectional shape. As compared to dynamic systems that include flexible cords and spacers, embodiments according to the present invention advantageously allow for elastic distraction or stretchability of the connecting member assembly and the use of closed and open-ended bone anchors, as well as fixed and polyaxial bone anchors.

OBJECTS AND ADVANTAGES OF THE INVENTION

Therefore, it is an object of the present invention to overcome one or more of the problems with bone attachment assemblies described above. An object of the invention is to provide dynamic medical implant stabilization assemblies having longitudinal connecting members that include an elastic inner core that allows for bending, torsion, compression and distraction of the assembly. Another object of the invention is to provide such an assembly wherein the elastic portion is insertable into a protective outer sleeve. A further object of the invention is to provide such an assembly wherein the outer sleeve may be compressed upon installation. A further object of the invention is to provide dynamic medical implant longitudinal connecting members that may be utilized with a variety of bone screws, hooks and other bone anchors, including fixed and polyaxial implants. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 11 is an enlarged exploded partial perspective view of the core of FIG. 1 shown with an alternative polyaxial bone screw.

FIG. 12 is an enlarged and partial perspective view of the assembly of FIG. 1 shown assembled with the polyaxial bone screw of FIG. 11 and with portions broken away to show the detail thereof.

DETAILED DESCRIPTION OF THE INVENTION

Figure 1:
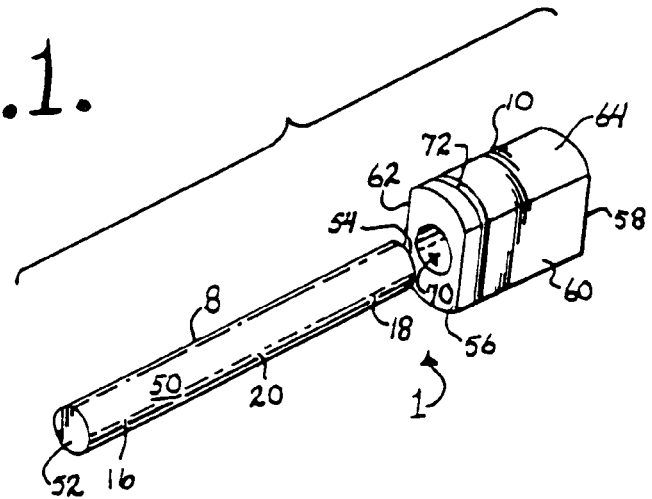
FIG. 1 is an exploded perspective view of a dynamic fixation connecting member assembly according to the invention including an elastic inner core and an outer sleeve.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words side, top, bottom, up and down, front and back and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-5, the reference numeral 1 generally designates a non-fusion dynamic stabilization longitudinal connecting member assembly according to the present invention. The connecting member assembly 1 includes an inner core 8 and an outer sleeve or spacer 10. The inner core 8 is elongate having a central longitudinal axis A and also including a first end portion or section 16, an opposite second end portion or section 18 and a mid-portion or section 20 with all of the portions 16, 18 and 20 extending along the axis A. It is foreseen that the inner core 8 may further include a small central lumen or through bore extending along the axis A for receiving a guide wire in a percutaneous or minimally invasive surgical procedure. The inner core 8 is receivable in the outer sleeve 10 with the outer sleeve 10 ultimately in position at the mid-portion or section 20.

Figure 4:
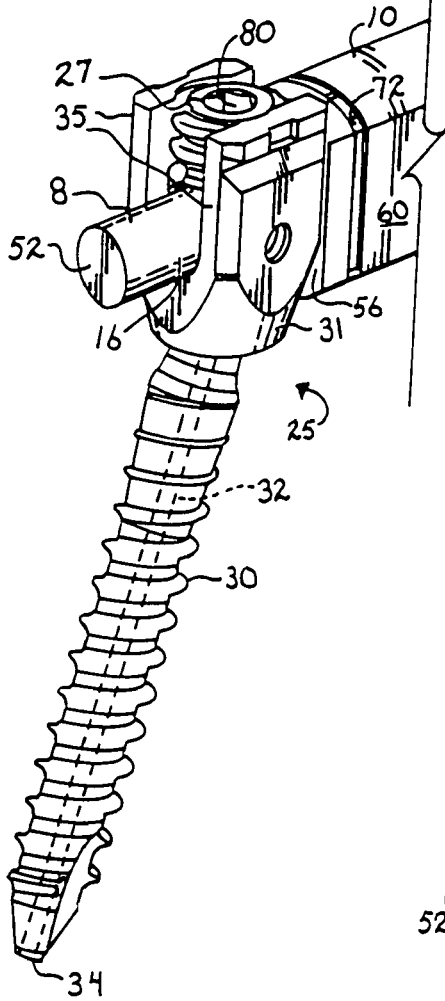
FIG. 4 is an enlarged and partial perspective view of the connecting member assembly of FIG. 1 shown with a polyaxial bone screw and cooperating closure member.
Figure 5:
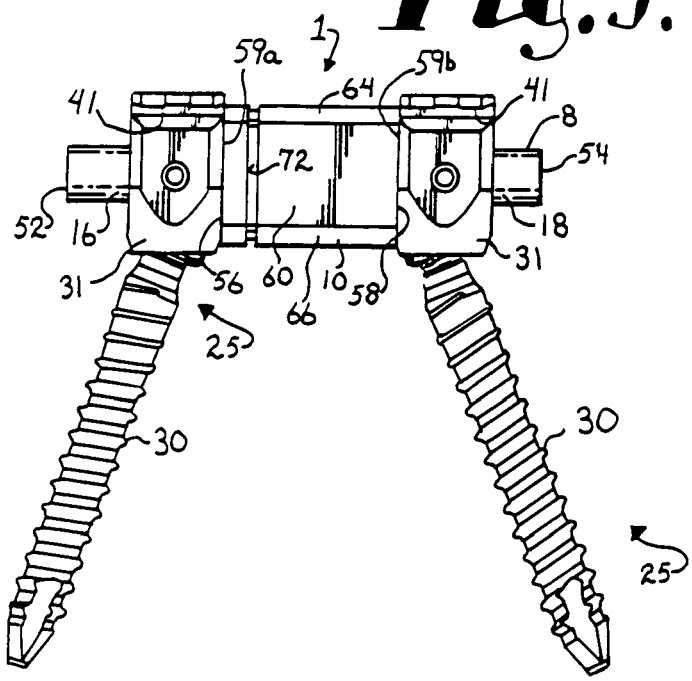
FIG. 5 is a front elevational view of the connecting member assembly as illustrated in FIG. 2 and further shown with a pair of polyaxial bone screws.

The dynamic connecting member assembly 1 cooperates with at least a pair of bone anchors, such as the polyaxial bone screws, generally 25 and cooperating closure structures 27 shown in FIGS. 4-5, the assembly 1 being captured and fixed in place at the end portions 16 and 18 by cooperation between the bone screws 25 and the closure structures 27. The sleeve 10 is sized and shaped for frictional engagement with each of a pair of bone screws 25 or other bone anchors, cooperating with the inner core 8 to support vertebrae adjacent thereto.

Because the end portions 16 and 18 are substantially solid, firm and cylindrical, the connecting member assembly 1 may be used with a wide variety of bone anchors already available for cooperation with more rigid rods including fixed, monoaxial bone screws, hinged bone screws, polyaxial bone screws, and bone hooks and the like, with or without upper and/or lower compression inserts or members, that may in turn cooperate with a variety of closure structures having threads, flanges, or other structure for fixing the closure structure to the bone anchor, and may include other features, for example, break-off tops and inner set screws. The bone anchors, closure structures and the connecting member assembly 1 are then operably incorporated in an overall spinal implant system for correcting degenerative conditions, deformities, injuries, or defects to the spinal column of a patient.

The polyaxial bone screws 25 illustrated in FIGS. 4 and 5 each include a shank 30 for insertion into a vertebra (not shown), the shank 30 being pivotally attached to an open receiver or head 31. The shank 30 includes a threaded outer surface and may further include a central cannula or through-bore 32 disposed along an axis of rotation of the shank, the through-bore 32 extending between a top surface and a bottom surface 34 of the shank 30. The bore 32 provides a passage through the shank interior for a length of wire or pin inserted into the vertebra prior to the insertion of the shank 30, the wire or pin providing a guide for insertion of the shank 30 into the vertebra.

The receiver 31 has a pair of spaced and generally parallel arms 35 that form an open generally U-shaped or squared shaped channel therebetween that is open at distal or front and back ends of the arms 35. The arms 35 each include radially inward or interior surfaces that have a discontinuous guide and advancement structure mateable with cooperating structure on the closure structure 27. The guide and advancement structure may be a partial helically wound flange form configured to mate under rotation with a similar structure on the closure structure 27 or a buttress thread, a square thread, a reverse angle thread or other thread like or non-thread like helically wound advancement structures for operably guiding under rotation and advancing the closure structure 27 downward between the receiver arms 35 and having such a nature as to resist splaying of the arms 35 when the closure 27 is advanced between the arms 35.

Each of the arms 35 also includes a V-shaped or undercut tool engagement groove 41 formed on a substantially planar outer surface thereof which may be used for holding the receiver 31 with a holding tool (not shown) having projections that are received within the grooves 41 during implantation of the shank 30 into the vertebra (not shown). The grooves 41 may also cooperate with a holding tool during bone screw assembly and during subsequent installation of the connecting member assembly 1 and the closure structure 27. It is foreseen that tool receiving grooves or apertures may be configured in a variety of shapes and sizes and be disposed at other locations on the receiver arms 35 for use with open and minimally invasive surgical techniques (MIS).

The shank 30 and the receiver 31 may be attached in a variety of ways. For example, a spline capture connection as described in U.S. Pat. No. 6,716,214, and incorporated by reference herein, may be used wherein the bone screw shank includes a capture structure mateable with a retaining structure disposed within the receiver. The retaining structure includes a partially spherical surface that is slidingly mateable with a cooperating inner surface of the receiver 31, allowing for a wide range of pivotal movement between the shank 30 and the receiver 31. It is also foreseen that the shank 30 and the retaining structure can be crimped or pinned together. Polyaxial bone screws with other types of capture and retaining connections may also be used according to the invention, including but not limited to camming and wedging connections, spherical connections, threaded connections, frictional connections utilizing frusto-conical or polyhedral capture structures, integral top or downloadable shanks, top and bottom loaded retainer rings that are integral, slotted or more than one piece, and the like. For example, with reference to FIGS. 11 and 12, a threaded connection is shown and is described in greater detail below. Also, as indicated above, polyaxial and other bone screws for use with connecting members of the invention may have bone screw shanks that attach directly to the connecting member or may include one or more pressure or compression members or inserts that cooperate with the bone screw shank, receiver and closure structure to secure the connecting member assembly to the bone screw and/or fix the bone screw shank at a desired angle with respect to the bone screw receiver that holds the longitudinal connecting member assembly. For example, with reference to FIGS. 11 and 12, both upper and lower pressure inserts are shown. Furthermore, although the closure structure 27 of the present invention is illustrated with the polyaxial bone screw 25 having an open receiver or head 31, it foreseen that a variety of closure structure may be used in conjunction with any type of medical implant having an open or closed head, including monoaxial bone screws, hinged bone screws, hooks and the like used in spinal surgery. It is foreseen that the front and back planar surfaces of the fixed screw heads can be convergent or divergent.

To provide a biologically active interface with the bone, the threaded shank 30 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With reference to FIGS. 11 and 12, the longitudinal connecting member 1 is shown cooperating with an alternative polyaxial screw assembly, generally 25A and a closure structure 27A. The polyaxial bone screw 25A includes a shank 30A for insertion into a vertebra (not shown), the shank 30 being pivotally attached to an open receiver or head 31A. The shank 30A includes a threaded outer surface and may further include a central cannula or through-bore disposed along an axis of rotation of the shank, the through-bore being similar to the bore 32 previously described herein with respect to the shank 30. The receiver 31A has a pair of spaced and generally parallel arms 35A that form an open generally U-shaped channel therebetween that is open at distal ends or front and back sides of the arms 35A. The arms 35A each include radially inward or interior surfaces that have a discontinuous guide and advancement structure mateable with cooperating structure on the closure structure 27A. The shank 30A and the receiver 31A are pivotally attached utilizing a retaining structure or ring 43 that threadably mates with the shank 30A. Furthermore a lower compression insert 44 and an upper compression insert 45 are received in the receiver 31A and closely receive, support and hold the core 8 of the longitudinal connecting member assembly 1. The shank 30A, the retaining structure 43 and the lower and upper compression inserts 44 and 45, respectively, are described in greater detail in U.S. patent application Ser. No. 11/522,503, filed Sep. 14, 2006, the disclosure of which is incorporated by reference herein. The receiver 31A further includes compression insert alignment and retention structures in the form of a pair of spring tabs 47. The tabs 47 cooperate with grooved or flat surfaces 48 on the lower compression insert 44 to hold the insert 44 in proper alignment with respect to the cylindrical core 8. The spring tabs 47 and cooperating insert surfaces 48 are described in greater detail in U.S. Provisional Patent Application Ser. No. 60/905,472 filed Mar. 7, 2007, the disclosure of which is incorporated by reference herein.

The longitudinal connecting member assembly 1 illustrated in FIGS. 1-5 and 11-12 is elongate, with the inner core 8 being an elastic substantially solid, somewhat firm, smooth and uniform cylinder or rod having an outer cylindrical surface 50 and a circular cross-section. The core 8 is made from natural or synthetic elastomers, including, but not limited to polyisoprene (natural rubber), and synthetic polymers, copolymers, and thermoplastic elastomers, for example, polyurethane elastomers, including polycarbonate-urethanes. It is foreseen that one portion or segment of the connecting member could be made from metal, etc. and affixed to the elastomer portion. The illustrated sleeve 10 is also made from a plastic, such as a thermoplastic elastomer, for example, polycarbonate-urethane having a greater stiffness than the elastomer of the core 8. In order to have low or no wear debris, the sleeve 10 inner surfaces and/or cooperating core 8 outer surfaces may be coated with an ultra thin, ultra hard, ultra slick and ultra smooth coating, such as may be obtained from ion bonding techniques and/or other gas or chemical treatments.

The illustrated core 8 has an end 52 and an opposite end 54, with the solid end portion 16 terminating at the end 52 and the solid end portion 18 terminating at the end 54. The portions 16 and 18 are each sized and shaped to be received in the U-shaped channel of a bone screw 25 with the mid-portion 20 sized and shaped to extend between cooperating bone screws 25. The sleeve 10 advantageously cooperates with the mid-portion 20, providing limitation and protection of movement of the core 8 at the portion 20. Thus, with reference to FIG. 5, the sleeve 10 is sized and shaped for substantially even and precise alignment and substantial frictional contact between flat end surfaces 56 and 58 of the sleeve 10 and cooperating flat planar side surfaces 59a and 59b of the receivers 31. The sleeve 10 can be cut to any length needed.

Furthermore, also with reference to FIGS. 5 and 12, and as will be discussed in greater detail below, when the sleeve 10 is implanted, and the closure structures 27 or 27A are tightened in place in the receivers 31 or 31A, the tools utilized to implant the assembly 1 and/or the bone screws 25 or 25A are manipulated to direct the pair of adjacent receivers 31 or 31A toward one another so as to axially compress the elastic sleeve 10 (now situated substantially coaxial with the core 8 axis A) between facing side surfaces, for example, surfaces 59a and 59b of the adjacent receivers 31 shown in FIG. 5. Such compression due to frictional engagement and compression of the sleeve 10 between the bone screw side surfaces 59a and 59b during installation results in some tension and distraction of the mid-portion 20 of the core 8 when the implantation tools are removed from the bone screws 25, as the sleeve end surfaces 56 and 58 then press against the facing bone screw surfaces 59a and 59b, but the core 8 is otherwise fixed with respect to each of the bone screws 25 within respective receiver 31 channels. Such dynamic tension/compression relationship between the sleeve 10 and the elastic core 8 provides further strength and stability to the overall assembly and also allows for the entire connecting member assembly 1 to elongate, if needed, in response to spinal movement. The increased stability and strength of the assembly advantageously allows for use of a smaller, more compact, reduced volume, lower profile longitudinal connecting member assembly 1 and cooperating bone anchors than, for example, flexible cord and spacer type longitudinal connecting member assemblies.

Figure 3:
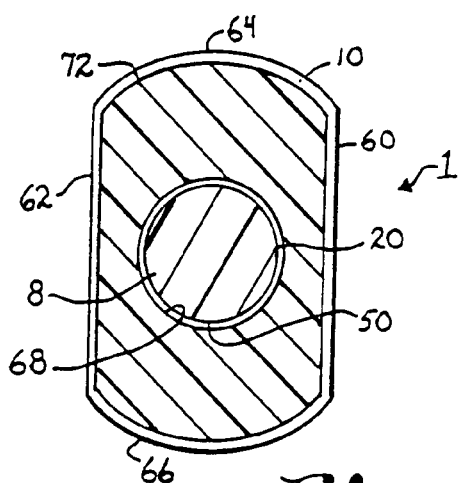
FIG. 3 is an enlarged cross-sectional view taken along the line 3-3 of FIG. 2.

The sleeve 10 further includes a pair of substantially flat parallel and opposite lateral surfaces 60 and 62 and a pair of curved opposite posterior/anterior surfaces 64 and 66. Each of the surfaces 60, 62, 64 and 66 extend between the flat end surfaces 56 and 58. The illustrated surfaces 64 and 66 have substantially the same radius originating along a central axis of the sleeve 10, such axis being coaxial with the axis A when the core 8 is inserted in the sleeve 10. As illustrated in FIG. 3, the geometry of the sleeve 10 allows for a narrower width between the parallel surfaces 60 and 62 than a distance or diameter between the curved surfaces 64 and 66. Such geometry provides adequate stiffness or support for the flexible core 8 in flexing due to the distance between the posterior/anterior curved surfaces 64 and 66, while the more narrow width or distance between the flat surfaces 60 and 62 allows for placement of the sleeve 10 between adjacent vertebrae without engagement with such vertebrae. Stated in another way, a cylindrical sleeve having a diameter large enough to produce a desired limit of bending or flexing movement of the core 8 would most likely have a diameter large enough to result in interference of the sleeve cylindrical surface with portions of adjacent vertebrae. The flat surfaces 60 and 62 allow for adequate clearance but do not detract from an overall strength of the sleeve 10.

Extending along the substantially central axis of the sleeve 10 (that corresponds to the axis A when the core 8 is disposed in the sleeve 10) is an internal substantially cylindrical and smooth surface 68. The surface 68 defines a bore 70 with a circular cross section, the bore 70 extending through the sleeve 10 and sized and shaped to receive the core 8. The internal surface 68 is of a slightly greater diameter than an outer diameter of the cylindrical surface 50 of the core 8, allowing for axially directed sliding movement of the sleeve 10 with respect to the core 8 during installation of the core 8 into the sleeve 10 and also when both the core 8 and the sleeve 10 are implanted with the sleeve 10 located between adjacent bone screws 25.

In the illustrated embodiment, the sleeve 10 further includes a compression groove 72. Sleeves 10 according to the invention may include one, none or any desired number of grooves 72. The groove 72 extends substantially uniformly about the sleeve 10 as illustrated in FIG. 3, being formed in the external surfaces 60, 62, 64 and 66 of the sleeve 10. The groove or grooves 72 may be added as desired to advantageously increase a longitudinal compressibility of the sleeve 10 during installation between a pair of bone screws 25 as previously described herein.

It is foreseen that the core 8 may be sized and shaped and made from such materials so as to provide for a relatively more rigid assembly 1 or a relatively more flexible assembly 1 with respect to flex or bendability along the assembly 1. Also, since the distance between the bone screw receivers or heads 31 can vary, the core 8 may need to be more or less stiff. Hybrid constructs are possible consisting of more rigid metals or PEEK material connected to less rigid elastic cores.

With reference to FIG. 4, the closure structure 27 can be any of a variety of different types of closure structures for use in conjunction with the present invention with suitable mating structure on the interior surface of the upstanding arms 35 of the receiver 31. The illustrated closure structure 27 is rotatable between the spaced arms 35, but could be a slide-in closure structure. The illustrated closure structure 27 is substantially cylindrical and includes an outer helically wound guide and advancement structure in the form of a flange form that may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 27 downward between the arms 35 and having such a nature as to resist splaying of the arms 35 when the closure structure 27 is advanced into the U-shaped channel formed by the arms 35. The illustrated closure 27 has an internal drive in the form of an aperture 80 utilized for assembly and removal of the closure 27. It is foreseen that the closure structure 27 may alternatively include an external drive, such as a break-off head designed to allow such a head to break from a base of the closure at a preselected torque, for example, 70 to 140 inch pounds. Such a closure structure would also include a base having an internal drive to be used for closure removal.

In use, at least two bone screws 25 or 25A are implanted into vertebrae for use with the longitudinal connecting member assembly 1. Each vertebra may be pre-drilled to minimize stressing the bone. Furthermore, when a cannulated bone screw shank is utilized, each vertebra will have a guide wire or pin (not shown) inserted therein that is shaped for the bone screw cannula, such as the cannula 32 of the bone screw shank 30, and provides a guide for the placement and angle of the shank 30 or 30A with respect to the cooperating vertebra. A further tap hole may be made and the shank 30 or 30A is then driven into the vertebra by rotation of a driving tool (not shown) that engages a driving feature (not shown) of the shank 30 or 30A. It is foreseen that the screws 25 or 25A and the longitudinal connecting member 1 can be inserted in a percutaneous or minimally invasive surgical manner.

Figure 2:
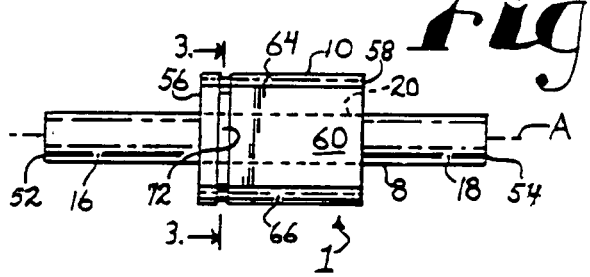
FIG. 2 is a front elevational view of the assembly of FIG. 1 shown assembled.

With particular reference to FIGS. 1 and 2, the longitudinal connecting member assembly 1 is assembled by inserting the core 8 into the bore 70 defined by the inner cylindrical surface 68 of the outer sleeve 10. In the illustrated embodiment, the end 54 of the core 8 is placed into the bore 70 at the surface 56 and the sleeve 10 is moved toward the end portion 16 until the sleeve 10 is positioned between the end portions 16 and 18 and is disposed about the mid-portion 20. It is noted that in the illustrated embodiment, the core 8 and the sleeve 10 may also be assembled in other ways, for example, by inserting the end 52 of the core 8 into the bore 70 at either the end surface 56 or the end surface 58.

With reference to FIGS. 4 and 5, the connecting member assembly 1 is eventually positioned in an open or percutaneous manner in cooperation with the at least two bone screws 25 with the sleeve 10 disposed between the two bone screws 25 and the end portions 16 and 18 each within the U-shaped channels formed by the arms 35 of the two bone screws 25. The sleeve 10 is positioned between the bone screws 25 with the flat surfaces 60 and 62 substantially aligned with the arms 35 of the receivers 31 and the curved surfaces 64 and 66 placed in posterior and anterior positions with respect to the patient's body. Because the sleeve 10 is substantially symmetrical, either the surface 64 or the surface 66 may be placed either anteriorly or posteriorly. In the illustrated embodiment, the surface 64 is in a posterior position facing away from the overall bone screw and connecting member assembly while the surface 66 faces anteriorly generally directed toward the bone screw shanks 30.

A closure structure 27 or 27A is then inserted into and advanced between the arms 35 or 35A of each of the bone screws 25 or 25A. The closure structure 27 or 27A is rotated, using a tool engaged with the inner drive 80 until a selected pressure is reached at which point the core 8 is urged toward, but not completely seated in the bone screw 27 or 27A channels. For example, about 80 to about 120 inch pounds pressure may be required for fixing the bone screw shank 30 or 30A relative to the respective receiver 31 or 31A.

In the embodiment illustrated in FIGS. 4-5, downward movement of the closure structure 27 into the channel 37 presses a respective end portion 16 or 18 downward into engagement with a top or other upper portion of the respective bone screw shank 30, pressing a structure that is fixed or integral with the shank 30 into engagement with an inner surface of the respective receiver 31, thus setting an angle of articulation of the respective shank 30 with respect to the respective receiver 31, clamping the shank 30 into a fixed position with respect to the receiver 31. The receiver 31 and shank 30 may thus be secured at any of a plurality of angles, articulations or rotational alignments relative to one another and within a selected range of angles both from side to side and from front to rear, to enable flexible or articulated engagement of the receiver 31 with the shank 30 until both are locked or fixed relative to each other.

Alternatively, with reference to FIGS. 11 and 12, upper and/or lower compression inserts may be provided to aid in holding the core 8 within the receiver 31A and fixing the shank 30A with respect to the receiver 31A. Furthermore, the assembly 1 may cooperate with an open receiver that is integral or fixed in position with respect to a bone screw shank or bone hook, or with a receiver having limited angular movement with respect to the shank, such as a hinged connection, also with or without other compression members or inserts for fixing the assembly 1, the receiver and/or the bone anchor in a desired position or orientation with respect to the cooperating vertebrae.

As indicated previously herein, with reference to FIG. 5, as the closure structures 27 are rotated and then tightened against the end portions 16 and 18 within a pair of spaced bone screws 25, such bone screws 25 may be pressed toward one another, the facing surfaces 59a and 59b being moved toward one another, thereby frictionally engaging and then compressing the sleeve 10 between the surfaces 59a and 59b. When the insertion and tightening tools are removed, the sleeve 10, pressing against facing surfaces 59a and 59b of the cooperating bone screw receivers 31, stretches the elastic mid-portion 20 of the core 8. The assembly 1 is thus substantially dynamically loaded and oriented relative to the cooperating vertebrae to provide relief (e.g., shock absorption) and protected movement with respect to flexion, extension, distraction and compressive forces placed on the assembly 1 and the two connected bone screws 25. The elasticity of the core 8 may also allow the core 8 to twist or turn along its axis providing relief for torsional stresses and torsional spring back. The sleeve 10 limits such torsional movement as well as bending movement of the core 8, providing spinal support. Furthermore, because the sleeve 10 is compressed during installation, the sleeve advantageously allows for some protected extension or distraction of both the core 8 and the sleeve 10, which is not possible with a tight, taut unyielding core, as well as compression of the assembly 1 in cooperation with the core 8.

If removal of the assembly 1 from any of the bone screws 25 or 25A is necessary, or if it is desired to release the assembly 1 at a particular location, disassembly is accomplished by using the driving tool (not shown) inserted in the aperture 80 to rotate and remove the closure structure 27 or 27A from the receiver 31 or 31A. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid metal or PEEK rod, having the same diameter as the inner core 8 end portions 16 and 18, utilizing the same or same sized receivers 31 or 31A and closure structures 27 or 27A. Alternatively, if less support is eventually required, a less rigid, more flexible assembly, for example, an assembly 1 made with a more flexible core 8, but with end portions having the same diameter as the inner core 8 end portions 16 and 18, may replace the assembly 1, also utilizing the same bone screws 25. Also, with reference to FIGS. 6-10 and described more fully below, the core 8 and cooperating sleeve 10 may be replaced with a more or less flexible core 8A, 8B, 8C, 8D or 8E having a different cross-sectional shape that is receivable in a sleeve having a similarly shaped through bore, as well as mating upper compression inserts.

It is foreseen that longitudinal connecting member assemblies according to the invention may be of a variety of lengths for cooperation with a plurality of bone screws 25. With reference to FIGS. 6-10, the assemblies may also have inner cores of a variety of shapes and sizes.

Figure 6:
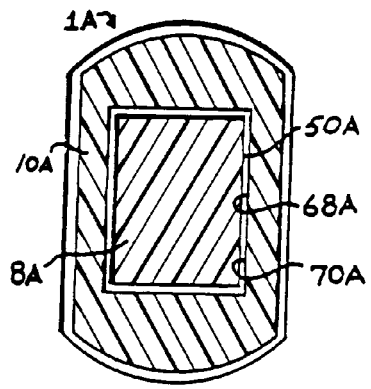
FIG. 6 is an enlarged cross-sectional view, similar to FIG. 3, showing a second embodiment of a dynamic fixation connecting member assembly according to the invention.

FIGS. 6-10 illustrate respective connecting member assemblies 1A, 1B, 1C, 1D and 1E that are identical or substantially similar to the assembly 1 with the exception of the outer dimension of the respective inner core and the inner through bore dimension of the respective slidingly mated sleeve. Unlike the assembly 1 that has a circular cross-section as shown in FIG. 3, the assemblies 1A, 1B, 1C, 1D and 1E have other cross-sectional shapes. In particular, FIG. 6 illustrates the assembly 1A that includes an inner core 8A and an outer sleeve 10A. The core 8A is substantially uniformly rectangular in cross-section, having four planar outer surfaces 50A. The outer sleeve 10A has four cooperating inner surfaces 68A that form a through bore 70A sized and shaped to closely receive the inner core 8A.

Figure 7:
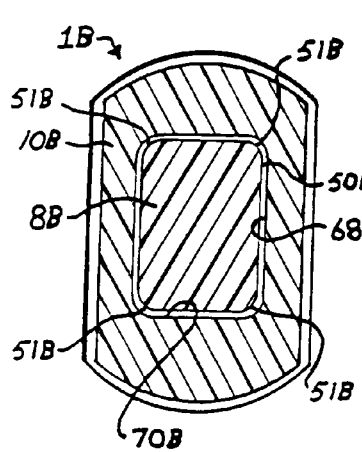
FIG. 7 is an enlarged cross-sectional view, similar to FIG. 3, showing a third embodiment of a dynamic fixation connecting member assembly according to the invention.

FIG. 7 illustrates the assembly 1B that includes an inner core 8B and an outer sleeve 10B. The core 8B is substantially uniformly rectangular in cross-section, having four planar outer surfaces 50B that intersect with one another at curved or rounded corners 51B. The outer sleeve 10B has four cooperating inner surfaces 68B that form a through bore 70B sized and shaped to closely receive the inner core 8A. The bore 70B is of rectangular cross-section and also has rounded corners to receive the rounded corners 51B of the inner core 8B.

Figure 8:
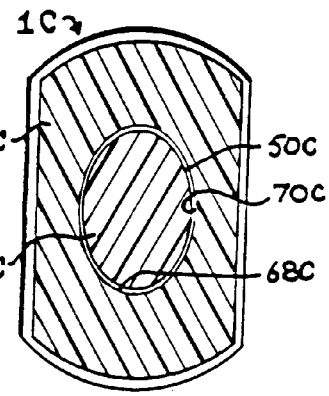
FIG. 8 is an enlarged cross-sectional view, similar to FIG. 3, showing a fourth embodiment of a dynamic fixation connecting member assembly according to the invention.

FIG. 8 illustrates the assembly 1C that includes an inner core 8C and an outer sleeve 10C. The core 8C is substantially uniformly oval or ellipsoidal in cross-section, having a curved outer surface 50C. The outer sleeve 10A has a cooperating curved inner surface 68C that forms a through bore 70C sized and shaped to closely receive the inner core 8C.

Figure 9:
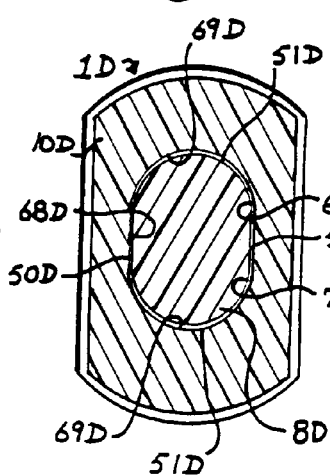
FIG. 9 is an enlarged cross-sectional view, similar to FIG. 3, showing a fifth embodiment of a dynamic fixation connecting member assembly according to the invention.

FIG. 9 illustrates the assembly 1D that includes an inner core 8D and an outer sleeve 10D. The core 8D includes a pair of opposed planar sides 50D and a pair of opposed curved sides 51D. The outer sleeve 10C has a pair of cooperating opposed planar surfaces 68D and a pair of cooperating opposed curved surfaces 69D that form a through bore 70D sized and shaped to closely receive the inner core 8D.

Figure 10:
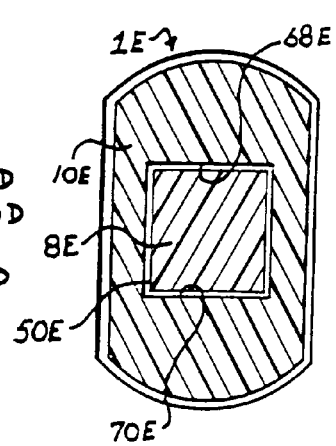
FIG. 10 is an enlarged cross-sectional view, similar to FIG. 3, showing a sixth embodiment of a dynamic fixation connecting member assembly according to the invention.

FIG. 10 illustrates the assembly 1E that includes an inner core 8E and an outer sleeve 10E. The core 8E is substantially uniformly square in cross-section, having four planar outer surfaces 50E. The outer sleeve 10E has four cooperating inner surfaces 68E that form a through bore 70E sized and shaped to closely receive the inner core 8E.

It is to be understood that while certain forms of the present invention have been illustrated and described herein, it is not to be limited to the specific forms or arrangement of parts described and shown.

What is claimed and desired to be secured by Letters Patent is as follows:

1. In a medical implant assembly having at least two bone anchors cooperating with a longitudinal connecting member, the improvement wherein the longitudinal connecting member comprises:
    a) an axially flexible and elastic inner elongate core having a substantially solid outer surface along an entire length thereof, the core extending completely through the at least two bone anchors and being under tension; at least one of the anchors includes a lower insert and a closure; and
    b) an elastic outer sleeve, the sleeve surrounding the core and extending between and being in compressive engagement with the at least two bone anchors.

2. The improvement of claim 1 wherein the sleeve is compressed along an elongate axis thereof.

3. The improvement of claim 1 wherein the elastic inner core is in tension along an elongate axis thereof.

4. The improvement of claim 1 wherein the sleeve is compressed between the bone anchors.

5. The improvement of claim 1 wherein the sleeve has at least one groove formed in an outer surface, the groove extending uniformly about the sleeve.

6. The improvement of claim 1 wherein the inner core has a circular cross-section.

7. The improvement of claim 1 wherein the inner core has an oval cross-section.

8. The improvement of claim 1 wherein the inner core has a polygonal cross-section.

9. In a medical implant assembly having at least two bone anchors cooperating with a longitudinal connecting member, the improvement wherein the longitudinal connecting member comprises:
    a) a flexible and elastic inner elongate core of one piece construction made from a plastic material, the core being attached directly to the at least two bone anchors under elastic tension to allow stretchability; at least one of the anchors includes a lower insert; and
    b) an elastic outer sleeve, the sleeve surrounding the core and extending between the two adjacent bone anchors and being sized and shaped for being in compressive engagement with an outer surface of each of the two adjacent bone anchors.

10. The improvement of claim 9 wherein the sleeve is compressed along an elongate axis thereof.

11. The improvement of claim 9 wherein the inner core is in tension along an elongate axis thereof.

12. The improvement of claim 9 wherein the sleeve is compressed along an elongate axis and the inner core is in tension along the elongate axis.

13. In a medical implant assembly having at least two bone anchors cooperating with a longitudinal connecting member, the improvement wherein the longitudinal connecting member comprises:
    a) a tensioned inner elongate core made from a flexible material of one piece construction and having a substantially smooth solid outer surface, the core being directly fixed to the at least two bone anchors and being elastically stretchable; and
    b) a compressed outer sleeve, the sleeve surrounding the core and extending between and compressively engaged with outer surfaces of the two adjacent bone anchors such that the core is in tension when the sleeve is in compression.

14. In a medical implant assembly having at least two bone anchors cooperating with a longitudinal connecting member, the improvement wherein the longitudinal connecting member comprises:
    a) a flexible and elastic inner elongate core having a substantially solid outer surface along an entire length thereof that is flexible along the length thereof, the core being attached directly to the two bone anchors so as to be under tension and elastically stretchable; at least one of the anchors includes a lower insert; and
    b) an outer sleeve, the sleeve surrounding the core and extending between the two bone anchors in compression such that the core is in tension and the sleeve is in compression.

15. The improvement of claim 1 wherein each of the bone anchors includes a channel for receiving the inner elongate core and a rotatable threaded closure for securing the inner elongate core within each respective bone anchor.

16. The improvement of claim 15 wherein each threaded closure directly engages the inner elongate core.

17. The improvement of claim 15 wherein at least one of the threaded closures includes a set screw.

18. The improvement of claim 15 wherein at least one of the threaded closures includes a break-off head.

19. The improvement of claim 15 further comprising an upper compression insert adapted for engaging both the closure and the elongate inner core.

20. The improvement of claim 19 wherein the upper compression insert is non-rotatable.

* * * * *